US010806874B2

(12) United States Patent
Zisser

(10) Patent No.: US 10,806,874 B2
(45) Date of Patent: Oct. 20, 2020

(54) COMPACT ATOMIZER

(71) Applicant: Michael Zisser, Berlin (DE)

(72) Inventor: Michael Zisser, Berlin (DE)

( * ) Notice: Subject to any disclaimer, the term of this patent is extended or adjusted under 35 U.S.C. 154(b) by 843 days.

(21) Appl. No.: 15/253,753

(22) Filed: Aug. 31, 2016

(65) Prior Publication Data

US 2017/0065780 A1 Mar. 9, 2017

(30) Foreign Application Priority Data

Sep. 8, 2015 (DE) .................. 20 2015 006 433 U
Apr. 27, 2016 (DE) ........................ 10 2016 006 438

(51) Int. Cl.
*A61M 15/08* (2006.01)
*A61M 15/02* (2006.01)
*A61M 16/14* (2006.01)
*A61M 15/00* (2006.01)

(52) U.S. Cl.
CPC .......... *A61M 15/085* (2014.02); *A61M 15/02* (2013.01); *A61M 16/142* (2014.02); *A61M 15/0091* (2013.01); *A61M 2205/0277* (2013.01); *A61M 2209/088* (2013.01); *A61M 2210/0618* (2013.01)

(58) Field of Classification Search
CPC .............. A61M 15/0091; A61M 15/02; A61M 15/085; A61M 16/142; A61M 2205/0277; A61M 2209/088; A61M 2210/0618; A61M 15/08; A62B 23/06
See application file for complete search history.

(56) References Cited

U.S. PATENT DOCUMENTS

| 2,277,390 | A | * | 3/1942 | Crespo | A61M 15/08 128/204.12 |
| 2,715,904 | A | * | 8/1955 | Hill | A61M 15/085 128/203.22 |
| 4,267,831 | A | * | 5/1981 | Aguilar | A61M 15/085 128/203.14 |
| 4,702,732 | A | * | 10/1987 | Powers | A61K 41/00 29/592.1 |
| 8,738,144 | B2 | * | 5/2014 | Schneider | A61N 1/326 607/127 |
| 2002/0123678 | A1 | * | 9/2002 | Lerner | A61K 9/0043 600/378 |
| 2003/0191426 | A1 | * | 10/2003 | Lerner | A61K 9/0009 604/20 |
| 2003/0204329 | A1 | * | 10/2003 | Marchitto | A61N 1/044 702/31 |
| 2006/0085027 | A1 | * | 4/2006 | Santin | A61M 31/00 606/199 |

(Continued)

FOREIGN PATENT DOCUMENTS

CN 2302810 Y * 1/1999
DE 4038546 A 6/1991

(Continued)

*Primary Examiner* — Kathryn E Ditmer
(74) *Attorney, Agent, or Firm* — Smartpat PLC

(57) ABSTRACT

A compact single-nostril atomizer for the inhalation of active ingredients is presented. The atomizer has an elastic U-shaped housing, a first end of which can be introduced into the nostril and a second end of which is formed as a clamping element. In the first end of the housing a cavity for receiving a reservoir is disposed. A reservoir containing an active ingredient can be inserted into the cavity.

15 Claims, 5 Drawing Sheets

(56) References Cited

U.S. PATENT DOCUMENTS

| | | | | |
|---|---|---|---|---|
| 2006/0224237 | A1* | 10/2006 | Furst | A61L 29/085 623/1.46 |
| 2010/0292756 | A1* | 11/2010 | Schneider | A61N 1/326 607/50 |
| 2012/0116325 | A1* | 5/2012 | Hunt | A61M 15/08 604/285 |
| 2014/0102049 | A1* | 4/2014 | Pacetti | A61L 31/16 53/476 |
| 2016/0058961 | A1* | 3/2016 | Haas | A61M 15/08 604/94.01 |

FOREIGN PATENT DOCUMENTS

| | | | | |
|---|---|---|---|---|
| DE | 102012011435 | A | 6/2013 | |
| DE | 102012011435 | A1* | 6/2013 | A61M 15/0003 |
| DE | 202013009326 | U1 | 12/2013 | |

* cited by examiner

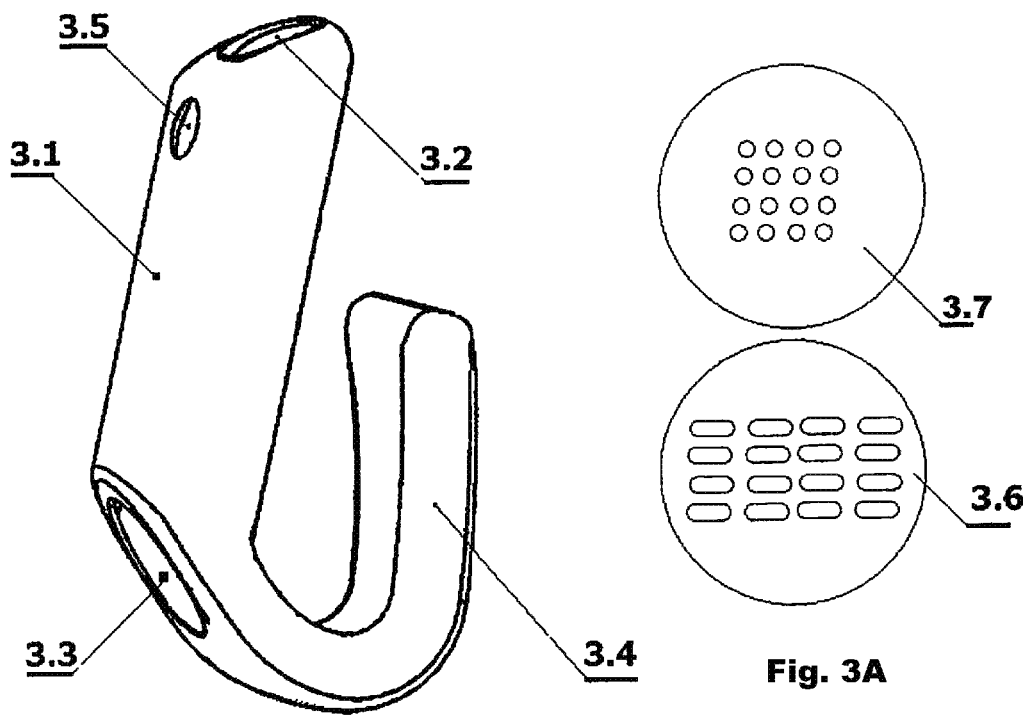
Fig. 3
Fig. 3A
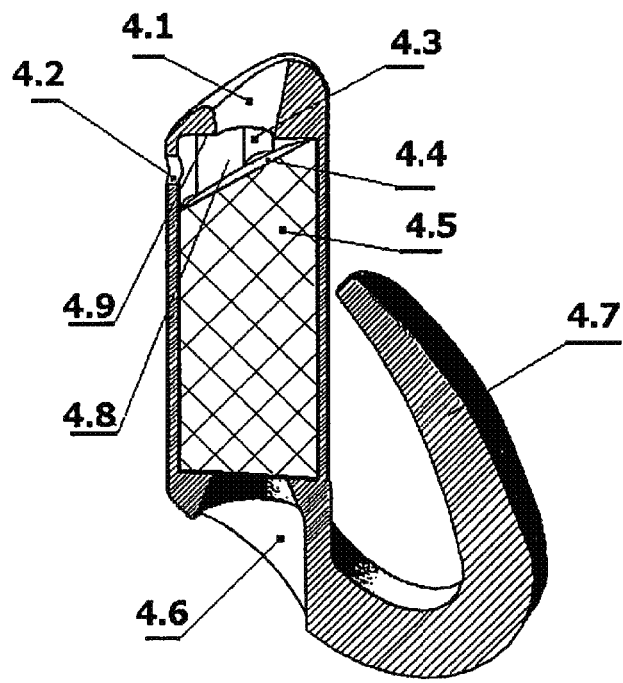
Fig. 4

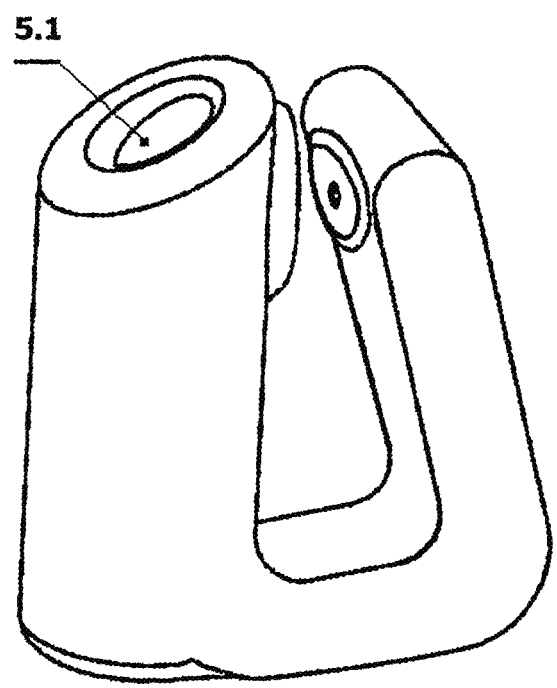
Fig.5
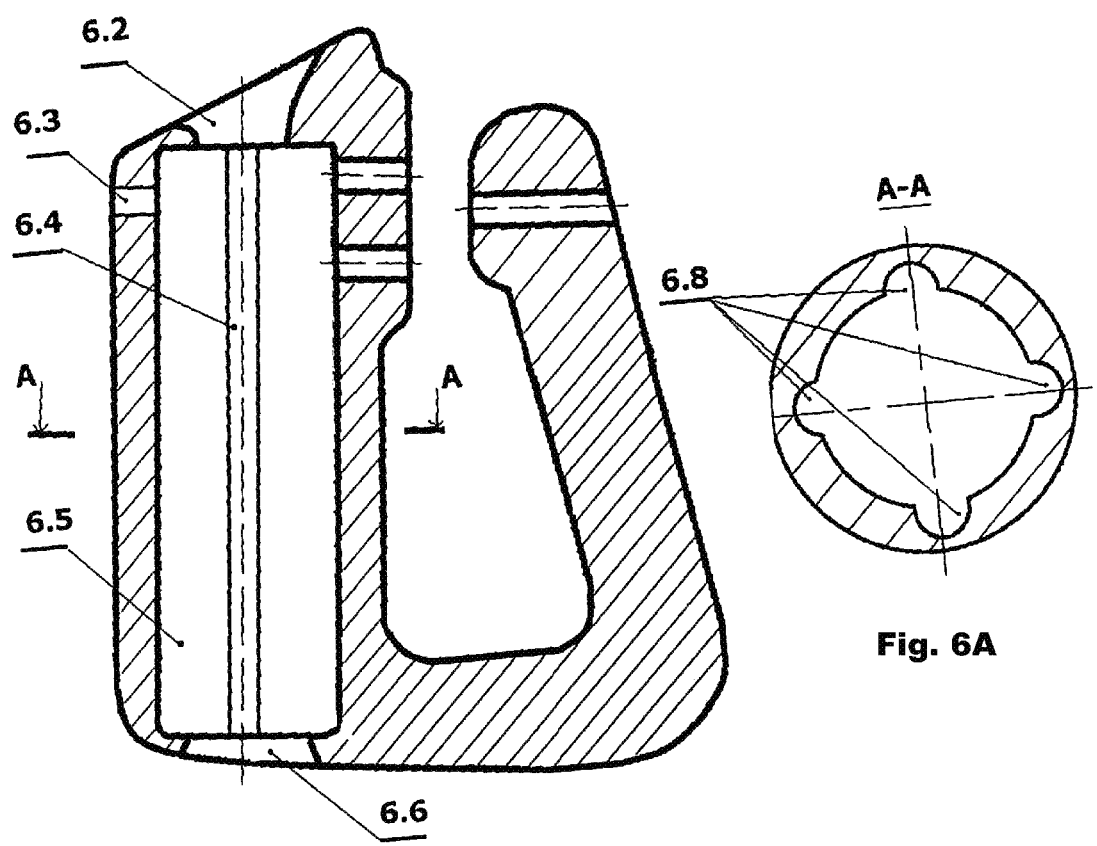
Fig. 6A
Fig. 6

COMPACT ATOMIZER

TECHNICAL FIELD

The present disclosure relates to a compact single-nostril atomizer for the inhalation of active ingredients.

BACKGROUND

Inhaling devices for insertion into a nostril are generally known. However, known devices have drawbacks in terms of their design. Often, the arrangement inside the nose is perceived as disadvantageous or disturbing to a user. Also, an active ingredient reservoir in known inhaling devices cannot be exchanged and known devices are not optimized for airflow.

Against this background, the object of the present invention is to optimize known compact atomizers. In addition, effective delivery of the active ingredient to be inhaled should be guaranteed in an advantageous way.

SUMMARY

An improved compact atomizer as described in this paper provides a better hold on the nose and lower optical conspicuousness than known devices. Its shape and the distance between a first end inside the nostril and a second end resting on the ala of the nose have been reduced to fit different nose shapes and to fit different size nostrils for men, women and children. The compact atomizer may be attached to one of the nasal passages. Elements of its housing are designed such that they minimize the foreign body sensation and enable maximum wearing comfort.

The improved atomizer eliminates disadvantages of known products. It works with a wider range of noses than similar products, including in the presence of a curved nasal septum. It prevents a change in the perception of odors and does not cause a change of intonation of a wearer's voice during use.

Additionally, the atomizer may utilize the action of micro-galvanic currents on the nasal mucosa and other tissue of the nose. This arises from the joint effect of metallic elements (electrodes) that are integrated into the compact atomizer and the current conducting electrolytic layer of the mucous membrane of the nasal wall.

A compact single-nostril atomizer comprises an elastic U-shaped housing having a first end which can be introduced into the nostril and a second end which is formed as a clamping element. A cavity for receiving a reservoir is disposed in the first end. Inserted into the cavity is a porous reservoir containing an active ingredient. The cavity may have an axial first outlet opening and a lateral second outlet opening. The axial first outlet opening may be tapered, having a smaller diameter on the inside than on the outside.

The atomizer may further comprise a reservoir opening through which the reservoir can be inserted into the cavity and removed from the cavity. The reservoir may contain an impermeable layer which prevents the active ingredient from escaping the reservoir. The impermeable layer may become permeable upon insertion of the reservoir into the cavity.

Within the cavity in the atomizer an evaporation area may be formed above the porous reservoir between an end face of the porous reservoir and an upper end of the cavity. Elongated grooves may be arranged along an interior surface of the cavity. The elongated grooves may extend upwardly into the evaporation area.

The atomizer may comprise an evaporation area which is formed above the porous reservoir between an upper end face of the porous reservoir and an upper end of the cavity. An axial first outlet opening may extend from the evaporation area through the first end of the elastic U-shaped housing. A lateral second outlet opening may extend from the evaporation area through a side wall of the elastic U-shaped housing, facing away from the second end. The porous reservoir may be a substantially cylindrical body having a slanted upper end, the upper end face of the porous reservoir being slanted downward towards the lateral second outlet opening.

The atomizer may further comprising a galvanic couple having a first electrode arranged at the first end and a second electrode arranged at the second end of the elastic U-shaped housing. Preferably, the first electrode and the second electrode are made of two different metals, for example gold and titanium. The first electrode and the second electrode are formed as rivets. Alternatively, the first electrode may be a ring-shaped member extending around the first end of the elastic U-shaped housing and the second electrode may be a ring-shaped member extending around the second end of the elastic U-shaped housing.

The atomizer may utilize a plurality of micro-indentations arranged on an outer surface of the first end of the elastic U-shaped housing. The micro-indentations may have an elongated shape whose long side is substantially perpendicular to a longitudinal axis of the cavity.

BRIEF DESCRIPTION OF THE DRAWINGS

FIG. 3 is a perspective view of an exemplary compact atomizer.

FIG. 3A shows optional outer surfaces of a compact atomizer

FIG. 4 is a cross-sectional view of the atomizer as in FIG. 3.

FIG. 5 is a perspective view of another embodiment of the compact atomizer.

FIG. 6 is a cross-sectional view of another exemplary compact atomizer.

FIG. 6A is a view taken from line A-A in FIG. 6

DETAILED DESCRIPTION

Figure 1:
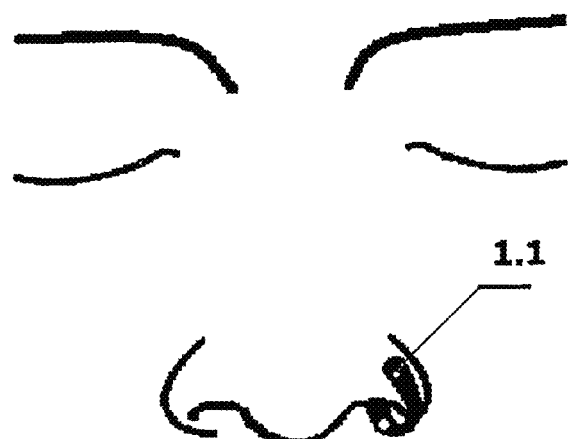
FIG. 1 shows a front view of the compact atomizer affixed to the nose.

Referring to FIG. 1, a compact single-nostril atomizer 1.1 for the inhalation of active ingredients is shown. The atomizer comprises a U-shaped housing having a first end which is inserted into the nostril of a user and a second end which holds onto the ala of the user's nose.

Figure 2:
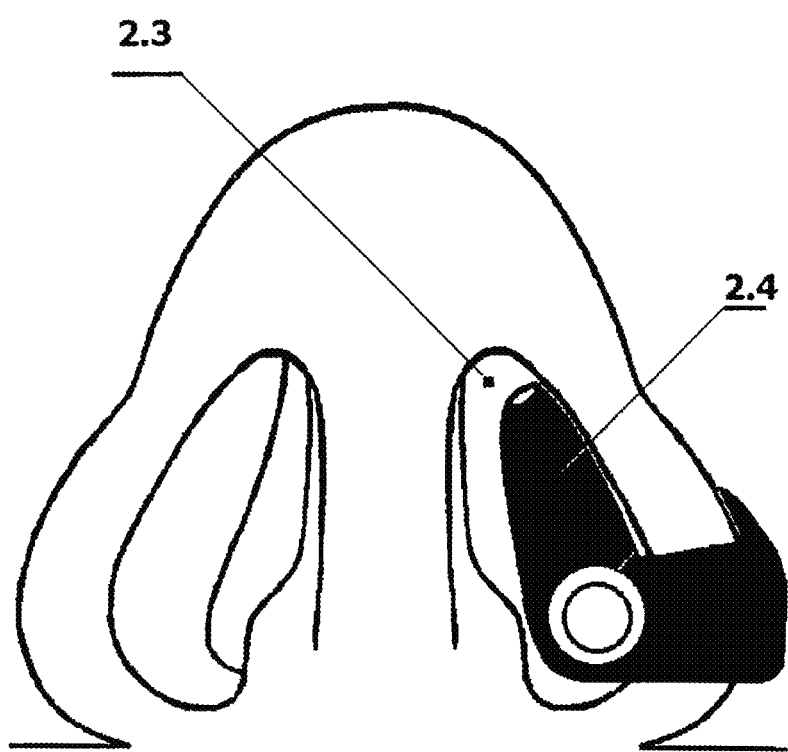
FIG. 2 shows a view from below of the compact atomizer affixed to the nose.
Figure 7:
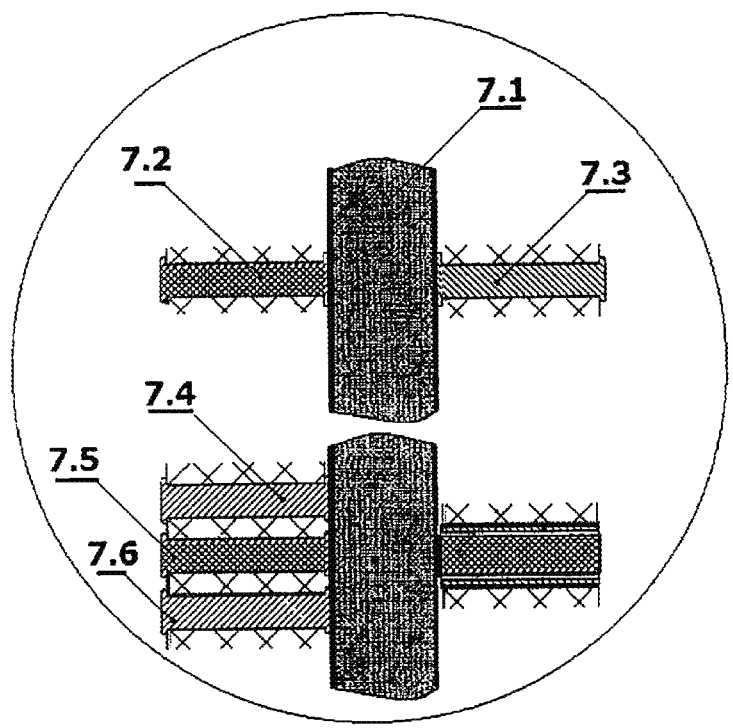
FIG. 7 shows a galvanic couple that may be used with the atomizer.
Figure 8:
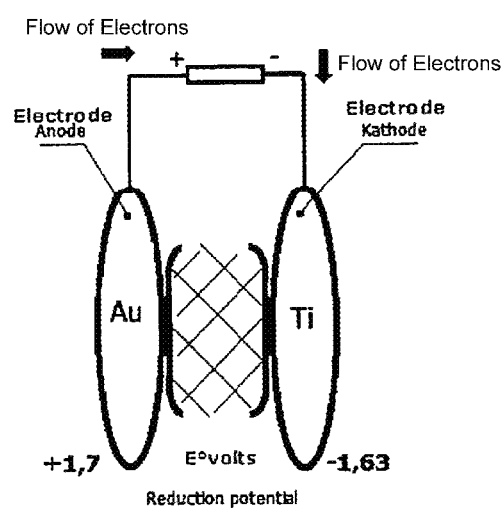
FIG. 8 is a schematic diagram of a galvanic couple that may be used with the atomizer.

FIG. 2 is a bottom view of the compact single-nostril atomizer 1.1, showing the atomizer inserted into the user's left nostril. The compact atomizer can be arranged in the nostril without causing discomfort in the area contacting the inner and the outer surface of the nose. As shown, the cross-sectional area 2.4 of the compact atomizer is significantly smaller than the cross-section of the nasal passage 2.3 in order not to negatively affect nasal breathing. The compact atomizer preferably covers less than 50% of the nasal passage area, and even more preferably less than 25% of the nasal passage area.

Referring to the cross-sectional views of FIG. 3 and FIG. 6, a compact atomizer for the inhalation of volatile active agents comprises an elastic U-shaped housing 3.0. A first end 3.1 of the housing 3.0 can be introduced into the nostril and a second end 3.4; 4.7 is formed as a clamping element with little pressure on the ala. The first end 3.1 comprises a cavity 6.5 for receiving a porous active ingredient reservoir 4.5 or a reservoir for volatile active ingredients. The cavity 6.5 comprises a first axial outlet opening 4.1 above the reservoir. In use, the first axial outlet opening 4.1 faces upward into the user's nasal cavity.

The cavity 6.5 is connected in the interior of the compact atomizer 1.1 to the at least one axial first outlet opening 4.1, preferably having a nozzle-like aperture. Preferably, therefore, the at least one outlet opening 4.1; 5.1; 6.2 being narrowed nozzle-like, runs axially extending from the cavity 6.5 of FIG. 6, thus having a nozzle-like aperture and expanding diffusion-like outwards.

At least one open-pored material 4.5 can be arranged in the cavity, wherein the cavity 6.5 inside the compact atomizer 1.1 is connected to the axial outlet opening 4.1 and has a nozzle-like aperture that is narrowed and expands diffusion-like outwards as shown in FIG. 4 and FIG. 6.

For the improvement and guidance of the escaping, volatile active ingredient, an evaporator area may have a lateral second outlet opening 3.5, 6.3. In use, the lateral second opening faces the user's columella.

The presence of additional continuous channels, of elongate recesses in the form of elongate grooves 4.3; 6.4; 6.8 along the longitudinal axis as shown in FIG. 6 is advantageous. The elongated grooves can serve as an additional reservoir. Thanks to these channels, the amount of the active ingredient escaping from the side walls of the reservoir in the evaporation area of the compact atomizer substantially increases. Further, it can be provided that the elongate grooves and the additional evaporation area are connected to each other in the interior of the cavity 4.8.

The compact atomizer is preferably made of a material which is approved for medical purposes. The compact atomizer exposes the contained ingredients without obstruction, through the axial first outlet opening 4.1 and the lateral second outlet opening 4.2 provided for this purpose. Thanks to this construction, the direction of the air currents is changed so that the dispersion released into the inhaled air is mainly directed to the inner side surface of the nasal wall.

The evaporation area is filled with an open-pore foam material and/or fibrous material 4.5, which allows the diffusion of volatile active ingredients. No fluids or only the smallest amount of aerosol can leak from the compact atomizer while it is not in use. The diffusion of the active ingredients occurs mainly when low air pressure is created in the area of the axial first outlet opening 4.1 and the lateral second outlet opening 4.2 during inhalation.

The reservoir area, in conjunction with the evaporation areas with the foam material and/or fibrous material arranged therein, thus the active ingredient reservoir, ensures a stable release of the active ingredients according to the type of porosity, that is, corresponding to the pore size and the distance between them. The porous or fibrous material must be stable and neutral with respect to all active ingredients with which it comes into contact. It is advantageous that the open-pore foam material and/or the fibrous material can be replaced after any time/use.

Another variant of using the construction of the active reservoir consisting of foam material and/or fibrous material is that this is packed compactly in a layer impermeable for this active ingredient and thus has an impermeable surface. The active ingredient reservoir can be inserted into the cavity by the user at any time as needed. Then the impermeable layer opens/unseals and is immediately available for use to the compact atomizer afterwards. This is an interchangeable active ingredient reservoir in which the active ingredient can escape in a controlled manner.

When inserting the replaceable drug reservoir 4.5 into the cavity 6.5 of the compact atomizer 1.1 through reservoir opening 3.3; 4.6; 6.6, the impermeable layer of the reservoir 4.5 according to FIG. 4 becomes permeable. This variant of construction permits not only prolonging the durability of the compact atomizer, but also enables its multiple use of the housing of the device whereby reservoirs can be filled with different active ingredients.

In another embodiment of the cavity 6.5, the compact atomizer has an additional evaporation area 4.8 in the interior of the compact atomizer, as shown in FIG. 4, which is formed by the front surface of the reservoir 4.4, which can form an angle relative to the axis of the cavity of the compact atomizer and the inner plane 4.9 of the axial first outlet opening 4.1. In this case, the open-pore foam material and/or fibrous material 4.5 has a material recess in the area of the axial first outlet opening 4.1 and the lateral outlet opening 4.2 and is preferably configured sloping in the direction of the lateral outlet opening 4.2 such that the open-pore foam material and/or fibrous material 4.5 slopes or the material recess reaches to below the lateral outlet opening 4.2.

Because of its miniaturization, the compact atomizer can be discreetly and aesthetically worn in public areas. It need not be removed while eating or while speaking and be worn over extended periods of time. The basic parameters of nasal breathing, that is, the resistance to the airflow produced by the compact atomizer, does not exceed the limit values of normal respiration. A suitable, medically harmless material for the compact atomizer can be an elastic silicone with hardness, for example, of 60-80 Shore.

The compact atomizer can be fastened on the nostrils by minimum pressure which does not exceed the pressure in the nasal capillaries. The elasticity of the material and the shape of the compact atomizer enable it to be comfortably and safely fastened in the nose while breathing.

Figure 9:
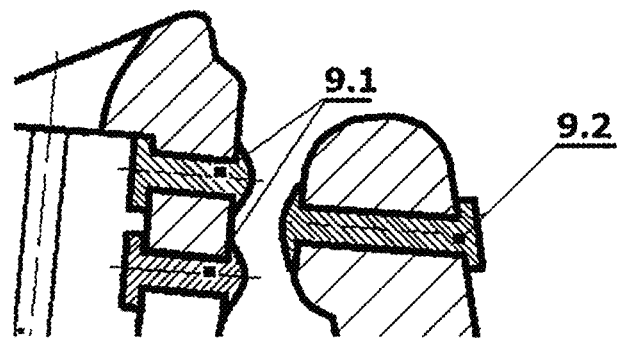
FIG. 9 shows an exemplary arrangement of electrodes on a compact atomizer.
Figure 10:
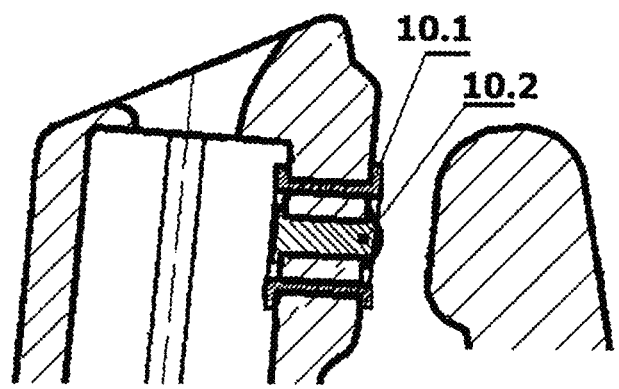
FIG. 10 shows an alternative exemplary arrangement of electrodes on a compact atomizer.
Figure 11:
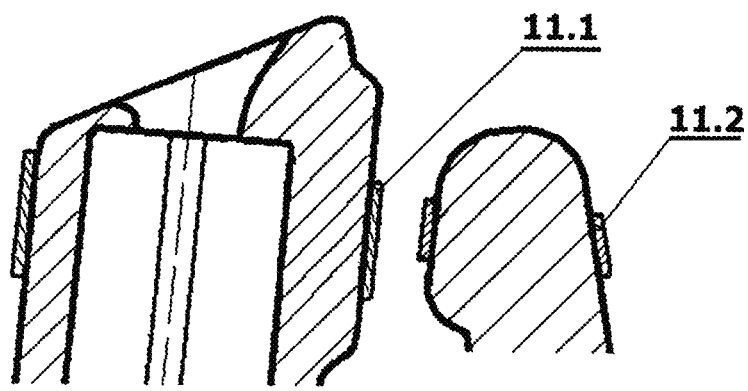
FIG. 11 shows yet another exemplary arrangement of electrodes on a compact atomizer.

As described, the compact atomizer may comprise a U-shaped housing 3.1 with a cavity 6.5 for receiving a porous active ingredient reservoir 4.5 or a reservoir for volatile active ingredients. The compact atomizer may further comprise a galvanic couple, wherein the galvanic couple comprises a first electrode arranged in the first end and a second electrode arranged in the second end as illustrated in FIG. 7, FIG. 9, FIG. 10, and FIG. 11. The first electrode is made of a different metal than the second electrode. The first electrode 9.1 and the second electrode 9.2 may be arranged adjacently on the first end and the second end of the U-shaped body as shown in FIG. 9. The first electrode 10.1 and the second electrode 10.2 may also be arranged concentrically on the first end of the U-shaped body as shown in FIG. 10. The first electrode and the second electrode may be designed as rivets.

Furthermore, it may be provided that numerous micro-indentations 3.6, 3.7 are located symmetrically or in any form on the outer surface of the compact atomizer 1.1 which is inserted into the nasal passage, wherein the micro-indentations 3.6 may have an elongated shape, wherein its long side is mostly perpendicular to the flow of the compact atomizer.

The end is provided with retaining beads in order to simultaneously reduce the pressure at the contact point of the housing of the compact atomizer and hold the compact atomizer securely in the nose according to FIGS. 1 to 6.

Referring to FIG. 9, FIG. 10 and FIG. 11, electrodes 9.1, 9.2, 10.1, 10.2, 11.1, 11.2 which are made of metal may be installed in the compact atomizer. The electrodes are part of an active galvanic element, which represents couples of metal electrodes that are immersed in a conductive electrolyte medium. The surface of the skin and mucous membranes are used as an electrolyte in the galvanic couple, and so are fluids throughout interior tissue which are saturated with various salts.

The electrolyte, a micro-conductive mucus of the nasal passage, and the mucosal surface of the skin form a conductor. Electrodes made of different metals are in contact with the skin and mucous membrane as illustrated in FIG. 7. As a result, the skin acts not only as an electrolyte in the galvanic couple, but also as conductor which enables the "electric resistance" between the electrodes. Consequently, as schematically shown in FIG. 8, it is the conductor which closes the electric circuit, thus any combination of two different metal electrodes and an electrolyte is called a galvanic couple and they serve as a direct voltage source. The chemical power source generates electricity by the direct conversion of chemical energy from redox reactions. In this case, the material of the contact metals that generate the known system of galvanic couples and corresponding currents between the electrodes on the skin surface and other tissues. The function of the galvanic cells as shown in FIG. 8 is based on a redox reaction. Reduction and oxidation proceed physically separated each in a half-cell (half element). The circuit is closed by connecting the two half-cells with an electron conductor and an ionic conductor.

If the pole is bridged by a galvanic conductor, a current of electrons from the negative to the positive pole results from the imposed voltage. A galvanic cell provides voltage until electrochemical equilibrium is reached. The electrodes of the galvanic couples 7.2, 7.4, 7.5, 7.6 can also be located on a side of the nasal passage. As shown in FIG. 10, the electrodes may be formed as concentrically arranged metallic contacts 10.1, 10.2 with the mucous membrane of the nasal passage. Then the galvanic currents flow locally between the surfaces of the metals that have different galvanic potential.

Referring to FIG. 8, a typical structure of a galvanic cell comprises two zones separated by a membrane (nostrils) with different body fluids as salt solutions (electrolyte). Each a body of the corresponding metal which is immersed in the solution (mucus, sweat) and preferably provides a surface. The membrane 7.1 prevents mixing of the salt solutions, but is permeable for charged particles when a charge imbalance between the solutions arises and is to be compensated. Bodies immersed in the half-chamber are called electrodes. The electrochemical potential that is formed between the metal and the electrolyte depends on the choice of the metal. With, for example, titanium, significantly more electrons/metal ion pairs are generated than with gold, so the negative charge on the titanium electrode is substantially greater than that on the gold electrode. The difference is the effective excess of negative charges on the titanium electrode with respect to those on the gold electrode. The titanium electrode is the negative pole, the gold electrode is the positive pole. The generated voltage may be 3.3 volts. This is called imposed voltage or open-circuit voltage.

The effect that creates the voltage is based on metal atoms dissipate on the boundary surfaces into positive metal ions which enter into solution and electrons that remain in the metal. The dissipation process into electrons/metal-ion couples is accompanied by a recombination process of the couples to atoms. Both seek an (electrochemical) equilibrium state in which the dissipation and recombination just cancel each other. If this equilibrium state is reached, there is a stable number of electrons/metal-ion couples that are collected at the boundary surface. Since they are stably separated, they generate a voltage (electrochemical potential.)

A variety of physical, chemical and biological processes must be considered when designing a compact atomizer to deliver active ingredients through the nasal membranes. Investigations of the sensitivity of the nasal mucosa of the nose showed particularly strong sensitivity in zones of tactile and painful irritation—the area of the tubercles on the nasal septum and the front ends of the lower and middle shells.

Considering the sensitivity to irritation and mechanosensitive trigeminal perception of the skin, olfaction and sensitivity, the stimulation with regard to mechanical irritation to highly sensitive nasal mucosa must be reduced during contact with the inhaler and direct contact with concentrated active ingredient must be prevented, since the mucosa of the upper respiratory tract is provided with many nerves, which have close reflex-like connections with near and distant organs and organ systems. Reflex reactions (sneezing, coughing) arise when the nasal mucosa are irritated.

A compact atomizer may interact with several functions of the nose:

Humidification—the nasal mucosa and breathing air by the nasal secretions. The action of a number of active ingredients enhances the activity of the mucous glands, which increases the humidity of the nasal passage significantly. This is an important physiological need for a normal nasal breathing.

Heating up—the breathing air by the warm blood in the vessels of the nasal mucosa. The action of some active ingredients causes an increased innervation of the tissue of the nasal passage and as a result the flow of blood in the capillaries of the tissue of the nasal passage.

Filter function—the strong hairs of the nasal vestibule are directed outward and provide protection against inhaled particles and other foreign objects of this size so that they do not even get into the nasal cavities. By bending the air stream, particles of the breathing air hit the mucosa, are deposited there in the nasal mucus and are carried away and swallowed into the throat via the surface of the mucosa with the nasal mucus within 30 minutes. Increasing the humidity of the nasal passage significantly improves its filtering function.

Olfaction. The perception of smells when using this compact atomizer with active ingredients is less suppressed than through known devices for similar purposes.

A compact atomizer may interact with the curvature of the nasal septum. The nasal septum can be bent stronger toward one of the two nasal cavities by different causes. Breathing through the affected nasal cavity is very difficult because the air passage is hindered by this malformation. When a bent nasal septum is present, one of the nasal passages is selected as a "Monoclip" for optimal use of the compact atomizer.

A compact atomizer may be used to deliver active ingredients. Liquid active substances may be those primarily of plant origin and have minimal or no side effects, such as, for example, essential oils, plant extracts, sometimes drugs. These active ingredients are defined as aids, preventive agents, preservatives and remedies that raise no objections from a physiological or therapeutic point of view, in order to be administered through the nose.

Essential aromatic oils in small doses are highly effective means of calming, regulating the activity of mucous membranes and mucous glands, for pain relief and can be used very well for the normalization of many physiological processes. In order to achieve the desired effect, the inhalation of small quantities of essential or aromatic oils, which are often used in aromatherapy or inhalation practice, is sufficient. Their effect is particularly effective when the diffusion of the substance occurs during breathing in which micro-doses are delivered continuously. Tests show that the concentration of the inhalation product which is delivered using a compact atomizer, and the concentration in the air volume of a breath is often not more than 0.00001%. Despite the very low concentration of the active ingredient, the reaction of the sensor systems of the respiratory system is sufficient for physiological and healing effects.

A compact atomizer may interact with the biochemistry of the nasal mucosa. The optimum pH concentration of the secretion of the nasal cavity is important for the preservation of the bactericidal properties of mucus, the activation of cilia of the ciliated epithelium, the vascular tone of the mucosal surface of the nasal cavity and has a particular importance for the safety of the protection and respiratory function of the nose. pH measurement results in the areas of the nose is between 5.7-7.2 pH with a maximum at 6.4-6.5 for the secretion of the nasal mucosa. Outside the nasal cavity, the pH of the secretion varies in the range 7.0-8.4 at the time, when directly in the nasal cavity, the pH of the secretion is 6.5-7.2. It is assumed that the mucus of the nasal cavity at pH—6.5 is sterile.

An optimum viscosity of the secretion is achieved at an ambient relative humidity of more than 80% and a temperature of 35° C.

A compact atomizer may interact with the hydrogen ion concentration on mucosal surfaces in the nose. The concentration of the hydrogen ions of the secretion on the mucosal surface of the nasal cavity reflects complex biochemical and physical-chemical processes that take place in the cells and fluids of the mucous membrane of the skin. The conversion of the secretion from sol into gel takes place at a pH value of 6.5 to 7.6 by the action of carbon dioxide of the respiratory air. After overcoming of airway inflammation, the pH reaction of the nasal mucosa becomes neutral very quickly, which is one of the criteria for determining the status of the nasal mucosa. The conversion of the secretion from the sol into the gel takes place at a pH-value from 6.5 to 7.6 by the action of carbon dioxide of the respiratory air.

A compact atomizer may generate healing galvanic micro-currents. Upon insertion of the clip into the nasal passage and upon contact of the metal electrodes to the mucus and the outer surface of the nose, the electrical circuit of the electrochemical cell is closed, whose purpose is to create therapeutic and physiological effects in the tissue of the nose, such as anti-inflammatory effects
analgesic effects
calming effect
effect of a dilation of blood vessels (causing an overfilling of the vessels of the circulatory system of the tissue of nasal passages with blood.)
effect which causes a lowering of the muscle tone
stimulating or inhibiting secretory effect Parallel voltages arise between the electrodes, an electrophoresis of ions and active ingredients takes place by inhalation in the zone of the nasal passage. Whereby as a result of the action of the galvanic cell of the clip, not only do galvanic currents arise in the skin tissue and stimulation of nerve endings occur, but also an enrichment of the tissue with metal ions is observed. With saturation of metal ions, control processes occur as a result of redox reactions and a process of micro-electrophoresis of metals in the tissue and the therapeutic effect of noble metal ions. Along with the movement of the ions, the electric current changes the permeability of the biological membranes and increases passive transport by these large protein molecules and other substances (phenomenon of electrical diffusion). When the current leads along the nerves, the metabolism accelerates. The direct current thus causes the following physico-chemical effects in biological tissues: electrochemical polarization, electrical diffusion and electro-osmosis.

Prolonged exposure to the contacts of the clip, which are made of different galvanic couples, is therefore a source of long-term impulses in the nerve centers. The study of the effects of discharge currents of the galvanic couple of the device shows that a slight warming of the applicator takes place.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

What is claimed is:

1. A compact single-nostril atomizer, comprising:
an elastic U-shaped housing having a first end which can be introduced into the nostril and a second end which is formed as a clamping element;
an elongated substantially cylindrical cavity disposed in the first end; and
a porous reservoir containing an active ingredient that is insertable into the elongated cavity further comprising a galvanic couple having a first electrode arranged at the first end of the elastic U-shaped housing and a second electrode arranged at the second end of the elastic U-shaped housing, wherein the first electrode and the second electrode are made of two different metals, and wherein at least a portion the first electrode and the second electrode are present on an outside of the housing of the elastic U-shaped housing such that the first electrode and the second electrode are configured to contact either side of a nasal ala of a user.

2. The atomizer as in claim 1, wherein an axial first outlet opening and a lateral second outlet opening are arranged at an upper end of the cavity.

3. The atomizer as in claim 2, wherein the axial first outlet opening is tapered, having a smaller diameter on an inside of the housing of the elastic U-shaped housing than on the outside of the housing of the elastic U-shaped housing.

4. The atomizer as in claim 1, further comprising a reservoir opening through which the porous reservoir can be inserted into the cavity and removed from the cavity, the reservoir opening being arranged at a lower end of the cavity.

5. The atomizer as in claim 4, wherein the porous reservoir comprises an impermeable layer which prevents the active ingredient from escaping the reservoir prior to insertion of the porous reservoir into the cavity.

6. The atomizer as in claim 1, wherein the cavity comprises an evaporation area which is formed above the porous reservoir between an end face of the porous reservoir and an upper end of the cavity.

7. The atomizer as in claim 6, further comprising elongated grooves which are arranged along an interior surface of the cavity.

8. The atomizer as in claim 7, wherein the elongated grooves extend upwardly into the evaporation area.

9. The atomizer as in claim 1, further comprising:
an evaporation area which is formed above the porous reservoir between an upper end face of the porous reservoir when the porous reservoir is inserted into the cavity and an upper end of the cavity;
an axial first outlet opening extending from the evaporation area through the first end of the elastic U-shaped housing; and
a lateral second outlet opening extending from the evaporation area through a side wall of the elastic U-shaped housing facing away from the second end,
wherein the porous reservoir is a substantially cylindrical body having a slanted upper end, the upper end face of the porous reservoir configured to slant downward towards the lateral second outlet opening when the porous reservoir is inserted into the cavity.

10. The atomizer as in claim 1, wherein the first electrode and the second electrode are formed as rivets.

11. The atomizer as in claim 1, wherein the first electrode is a ring-shaped member extending around the first end of the elastic U-shaped housing and the second electrode is a ring-shaped member extending around the second end of the elastic U-shaped housing.

12. The atomizer as in claim 1, further comprising a plurality of micro-indentations arranged on an outer surface of the first end of the elastic U-shaped housing.

13. The atomizer as in claim 12, wherein the micro-indentations have an elongated shape and whose long side is substantially perpendicular to a longitudinal axis of the cavity.

14. A compact single-nostril atomizer, comprising:
an elastic U-shaped housing having a first end which can be introduced into the nostril and a second end which is formed as a clamping element;
an elongated cavity disposed in the first end; and
a porous reservoir containing an active ingredient arranged within the elongated cavity, the porous reservoir container being insertable into and removable from the elongated cavity through an axial opening of the elongated cavity in the elastic U-shaped housing, further comprising a galvanic couple having a first electrode arranged at the first end of the elastic U-shaped housing and a second electrode arranged at the second end of the elastic U-shaped housing, wherein the first electrode and the second electrode are made of two different metals, and wherein at least a portion the first electrode and the second electrode are present on an outside of the housing of the elastic U-shaped housing such that the first electrode and the second electrode are configured to contact either side of a nasal ala of a user.

15. The atomizer as in claim 14,
wherein a diameter of the axial opening is smaller than a diameter of the porous reservoir.

* * * * *